(12) United States Patent
Tsukada et al.

(10) Patent No.: US 7,759,931 B2
(45) Date of Patent: Jul. 20, 2010

(54) DEVICE FOR MEASURING MAGNETIC IMPEDANCE

(75) Inventors: Keiji Tsukada, Okayama (JP); Toshihiko Kiwa, Okayama (JP)

(73) Assignee: National University Corporation, Okayama University, Okayama (JP)

( * ) Notice: Subject to any disclaimer, the term of this patent is extended or adjusted under 35 U.S.C. 154(b) by 28 days.

(21) Appl. No.: 11/886,074

(22) PCT Filed: Mar. 13, 2006

(86) PCT No.: PCT/JP2006/304927
§ 371 (c)(1),
(2), (4) Date: Oct. 11, 2007

(87) PCT Pub. No.: WO2006/109382
PCT Pub. Date: Oct. 19, 2006

(65) Prior Publication Data
US 2008/0211492 A1 Sep. 4, 2008

(30) Foreign Application Priority Data
Mar. 14, 2005 (JP) ............................. 2005-071383

(51) Int. Cl.
*G01R 33/12* (2006.01)
(52) U.S. Cl. .................. 324/235; 324/243; 340/551
(58) Field of Classification Search .......... 324/228–253
See application file for complete search history.

(56) References Cited

U.S. PATENT DOCUMENTS 3,450,986 A * 6/1969 Chapman et al. ............ 324/235

(Continued)

FOREIGN PATENT DOCUMENTS

JP B1 46-10635 3/1971

(Continued)

OTHER PUBLICATIONS

Hart, Lynn W. et al., "A Noninvasive Electromagnetic Conductivity Sensor For Biomedical Applications," Transactions on Biomedical Engineering, vol. 35, No. 12, pp. 1011-1022, Dec. 1988.

(Continued)

*Primary Examiner*—Jay M Patidar
(74) *Attorney, Agent, or Firm*—Oliff & Berridge, PLC (57) ABSTRACT

The present invention relates to a magnetic impedance measurement device comprising an apply coil for generating an alternate magnetic field of variable frequency, a power source for the apply coil, at least one magnetic sensor means comprising a pair of magnetic sensors for detecting orthogonal vector components of a magnetic field generated from a test object, the vector components being parallel to the face of the apply coil, a measurement means for the magnetic sensor for measuring a detected signal from said magnetic sensor mean, the measurement means being located at a distance from the face of the apply coil and facing the test object, a lock-in amplifier circuit for detecting from an output of the measurement means a signal having the same frequency as the frequency of the apply coil and an analysis means for analyzing intensity and phase changes of an output of the magnetic sensor means with the use of an output signal of the lock-in amplifier circuit.

16 Claims, 3 Drawing Sheets

U.S. PATENT DOCUMENTS

| | | | |
|---|---|---|---|
| 3,579,099 A * | 5/1971 | Kanbayashi | 324/235 |
| 4,668,913 A * | 5/1987 | Vinal | 324/235 |
| 5,446,379 A * | 8/1995 | Machi | 324/240 |
| 6,232,774 B1 * | 5/2001 | Kimura | 324/235 |
| 6,404,192 B1 | 6/2002 | Chiesi et al. | |

FOREIGN PATENT DOCUMENTS

| | | |
|---|---|---|
| JP | A 5-203629 | 8/1993 |
| JP | A 7-311251 | 11/1995 |
| JP | A 9-178710 | 7/1997 |
| JP | A 2001-13231 | 1/2001 |
| JP | A 2003-4831 | 1/2003 |
| JP | A 2003-199723 | 7/2003 |
| JP | A 2003-222664 | 8/2003 |

OTHER PUBLICATIONS

Hatsukade, Yoshimi et al., "Non-Contact SQUID-NDT Method Using A Ferrite Core For Carbon-Fibre Composites," Superconductor Science and Technology, vol. 15, pp. 1728-1732, 2002.

Kandori, Akihiko et al., "Two-Dimensional Mapping Of Impedance Magnetocardiograms," Transactions on Biomedical Engineering, Vo. 49, No. 7, pp. 721-728, Jul. 2002.

Tsukada, Keiji et al., "Multichannel SQUID System Detecting Tangential Components Of The Cardiac Magnetic Field," Rev. Sci. Instrum., vol. 66, No. 10, pp. 5085-5091, Oct. 1995.

* cited by examiner

DEVICE FOR MEASURING MAGNETIC IMPEDANCE

FIELD OF THE INVENTION

The present invention relates to a device for applying an alternate magnetic field to a test object and detecting a response characteristic thereof using a magnetic sensor.

BACKGROUND OF THE INVENTION

A metal detector is known as a device for applying an alternate magnetic field to examine the response characteristics. The metal detector comprises a search coil that generates an alternate magnetic field to generate an eddy current on a metal surface of the test object, which in turn generates a magnetic field repulsive to the applied magnetic field. Since this magnetic field changes an electromotive force in response to changes in the magnetic flux penetrating through the search coil, as may be represented using Faraday's law of electromagnetic induction, existence of metal can be detected by measuring the changes in a signal. Also known are methods of nondestructive inspection such as a method for inspecting a defect in a steel pipe or a wire rope by generating an eddy current in the same manner as in the case of the metal detector. Among applied examples of the metal detector are a metal detection gateway for preventing dangerous articles from being carried in for the purpose of terrorism prevention or crime prevention and a device for detecting a piece of metal, a needle for example, having been misplaced during manufacture in articles such as meat or clothes.

As a method for testing electrical characteristics of a living body, there is the bioelectrical impedance method in which an electrode is attached on the skin to apply a feeble alternate current to measure the impedance thereof. The method is most commonly used in body fat meters. Meanwhile, a method of applying, instead of applying current from an electrode, an alternate magnetic field to a human body to generate an induced current which in turn is detected by means of a search coil is disclosed as the magnetic bioelectrical impedance method in *A Noninvasive Electromagnetic Conductivity Sensor for Biomedical Applications* by Lynn W. Hart, et al., IEEE Transactions on Biomedical Engineering, Vol. 35, No. 12 (1988) pp. 1011-1021 (nonpatent reference 1).

Nonpatent reference 1: *A Noninvasive Electromagnetic Conductivity Sensor for Biomedical Applications* by Lynn W. Hart, et al., IEEE Transactions on Biomedical Engineering, Vol. 35, No. 12 (1988) pp. 1011-1021

In any of these detection methods, use is made of such search coils that capture the component of a magnetic field in the direction vertical to the apply coil face. Accordingly, it is only a change of a magnetic characteristic caused by a change in the induced current due to the material characteristic that can be captured during detection.

In Japanese Patent Application Laid-Open No. 2003-199723 (patent reference 1), there is disclosed a method for estimating the current density or the electric conductivity of a conductive material, in which an induced current is generated with a magnetic field or a current is directly applied, and also disclosed is a method for making an analysis with the use of a vectorial magnetic sensor.

Patent reference 1: Japanese Patent Application Laid-Open No. 2003-199723

As a method for nondestructive inspection for inspecting a defect in a metal material, there is known a method of generating an eddy current and measuring a magnetic field generated therefrom by means of a detector coil, the method being referred to as, for example, eddy current flaw detection. The detector coil detects as a component of the magnetic field to be measured the component parallel to the central axis of the magnetic field apply coil. In Japanese Patent Application Laid-Open No. H5-203629 (patent reference 2), it is disclosed that use is made of, as a detector coil placed inside the apply coil, a coil that detects the component of the magnetic field in the direction vertical to the central axis, since the impedance of the detector coil may be influenced, for example, by the material characteristic of the test object and the distance.

Patent reference 2: Japanese Patent Application Laid-Open No. H5-203629

A method of measuring the current distribution for the purpose of inspecting a defect in metal or plate materials made of carbon fiber is disclosed in *Non-contact SQUID-NDT method using a ferrite core for carbon-fibre composites* by Y. Hatsukade, et al., Superconductor Science and Technology, Vol. 15 (2002) pp. 1728-1732 (nonpatent reference 2). In this method, opponent polarities are applied onto the test object at a distance from each other to apply a magnetic field and a current is strongly induced in the test object between the opponent poles. As for the direction of a component of the magnetic field to be measured, measurement is made by means of a superconducting quantum interference device (SQUID) as a magnetic sensor for a difference in the same direction as that of an applied magnetic field and in the direction perpendicular thereto. Thus, an induced current is generated only in proximity to the magnetic sensor, and an image is created by synthesizing the currents having been measured at different measuring points on the test object.

Nonpatent reference 2: *Non-contact SQUID-NDT method using a ferrite core for carbon-fibre composites* by Y. Hatsukade, et al., Superconductor Science and Technology, Vol. 15 (2002) pp. 1728-1732

A method is disclosed in *Two-Dimensional Mapping of Impedance Magnetocardiograms* by A. Kandori, et al., IEEE Transactions on Biomedial Engineering, Vol. 49, No. 7 (2002) pp. 721-728 (nonpatent reference 3), in which an electrode is directly attached to a living body to apply a current and a magnetic field generated therefrom is measured by means of a SQUID. In this measurement, there is provided a coil for detecting a component of the magnetic field in the direction perpendicular with respect to the test object, and a component of the magnetic field similar to that in the case of metal detection or the magnetic bioelectrical impedance method is detected. Here, because there are magnetic fields entering into the detector coil as well as the magnetic field from the living body, the detector coil is provided with a cancel coil.

Nonpatent reference 3: *Two-Dimensional Mapping of Impedance Magnetocardiograms* by A. Kandori, et al., IEEE Transactions on Biomedial Engineering, Vol. 49, No. 7 (2002) pp. 721-728

Further, there is disclosed a method for inspecting the current distribution in a human body in *Multichannel SQUID system detecting tangential components of the cardiac magnetic field* by K. Tsukada, et al., Review of Scientific Instruments, Vol. 66, No. 10 (1995) pp. 5085-5091 (nonpatent reference 4), in which an image of the current distribution can be created by detecting each of orthogonal x and y components of the magnetic field, the xy plane being parallel to the body surface. In this method, however, it is a current autonomously flowing due to electrophysiological phenomena in the cardiac muscle that is to be measured and a current is not induced in the living body, and a change of the electrical impedance of a living body cannot be measured.

Nonpatent reference 4: *Multichannel SQUID system detecting tangential components of the cardiac magnetic field* by K. Tsukada, et al., *Review of Scientific Instruments*, Vol. 66, No. 10 (1995) pp. 5085-5091

DISCLOSURE OF THE INVENTION

Problems to be Solved

With the conventional modes of metal detectors, it is only the presence or absence of metal that is to be measured, and a local change of the impedance as an electrical characteristic of the test object is not specifically captured. With the magnetic bioelectrical impedance method, in the same way, it is also a change of the impedance as a whole that is to be captured, and a change in the current distribution inside the body due to a local change of the impedance cannot be inspected.

Moreover, with the method of directly measuring the vectorial components to estimate the current source, phase changes due to influences of the applied magnetic field or local impedance characteristics of the magnetic field generated from the test object cannot be measured because various interfering factors are not eliminated during a measurement.

Further, with the arrangement including a coil provided inside the apply coil for detecting the horizontal component in the eddy current flaw detection, measurement is problematically made only of a weak part of the eddy current when the test object is close, because the apply coil and the detector coil is in the same plane and the intensity of the magnetic field is weaker at the center of the coil in the applied magnetic field. Also, the distribution of the applied magnetic field varies problematically in different measurements when measurements are made with scanning movement so as to measure the current distribution of the test object in whole, because the apply coil and the detector coil are in the same plane. Thus, the distribution of current in the test object cannot be measured in whole.

In nondestructive inspections with the use of a SQUID as a magnetic sensor, also, it is not possible to induce a current in the whole test object and inspect the current distribution, since an alternate magnetic field is only applied in a localized portion to generate a current in that limited portion. In addition, because a signal of the applied magnetic field is entering into the magnetic sensor, use of a derivation coil, for example, is required as a cancel means.

Means for Solving the Problems

The present invention relates to a magnetic impedance measurement device comprising:

an apply coil for generating an alternate magnetic field of variable frequency, an exciting power source for exciting said apply coil, at least one magnetic sensor means including a pair of magnetic sensors for detecting orthogonal vector components (X, Y) of a magnetic field generated from a test object, the vector components (X, Y) being parallel to the face of the apply coil, a detector means for detecting a signal of said magnetic sensor means, the detector means being located at a distance from the face of the apply coil and in proximity to said test object and a measurement means for measuring a detected signal having been detected by said detector means.

The present invention relates to a magnetic impedance measurement device comprising:

an apply coil for generating an alternate magnetic field of variable frequency, an exciting power source for exciting said apply coil, at least one magnetic sensor means including a pair of magnetic sensors for detecting orthogonal vector components (X, Y) of a magnetic field generated from a test object, the vector components (X, Y) being parallel to the face of said apply coil, a detector means for detecting a signal of said magnetic sensor means, the detector means being located at a distance from said face of the apply coil and being movable so as to approach said test object and a measurement means for measuring a detected signal having been detected by said detector means.

The present invention relates to a magnetic impedance measurement device comprising:

an apply coil for generating an alternate magnetic field of variable frequency, an exciting power source for exciting said apply coil, at least one magnetic sensor means including a pair of magnetic sensors for detecting orthogonal vector components (X, Y) of a magnetic field generated from a test object, the vector components (X, Y) being parallel to said plane of the apply coil, a detector means for detecting a signal of said magnetic sensor means, the detector means being located at a distance from the plane of said apply coil and in proximity to said test object, a measurement means for measuring a detected signal having been detected by said detector means and a display means for analyzing a measured signal having been measured by said measurement means and performing an image processing for the measured signal and displaying the processed image.

The present invention relates to the magnetic impedance measurement device, the device further comprising a lock-in amplifier circuit for detecting from an output of said measurement means a signal having the same frequency as that of said apply coil.

The present invention relates to the magnetic impedance measurement device, the device further comprising an analysis means for analyzing intensity and phase changes of an output of said magnetic sensor means with the use of an output signal of said lock-in amplifier circuit.

The present invention relates to the magnetic impedance measurement device, the device further comprising an imaging means for imaging an induced current in said test object and a display means for displaying an output from the imaging means.

The present invention relates to the magnetic impedance measurement device, the device further comprising an abnormality determination means for determining an abnormal current with respect to a normal current distribution.

The present invention relates to the magnetic impedance measurement device, the device further comprising a scanning means for moving said test object in a direction parallel to or in directions parallel and vertical to the face of the apply coil as well as for fixing the test object.

The present invention relates to the magnetic impedance measurement device, wherein a plurality of said magnetic sensor means each including a pair of magnetic sensors are provided, the magnetic sensor means being located at an equal distance from each other.

The present invention relates to the magnetic impedance measurement device, wherein a composite magnetic field of a plurality of frequencies is generated at said apply coil by means of said power source for the apply coil and said lock-in amplifier circuit is provided for each of the plurality of frequencies.

The present invention relates to the magnetic impedance measurement device, wherein said apply coil is a pair of opposed-type apply coils and said test object is placed between said opposed apply coils.

The present invention relates to the magnetic impedance measurement device, wherein said magnetic sensor means is a Hall sensor, a magnetoresistive sensor, a magnetic impedance effect sensor, a flux gate or a superconducting quantum interference device.

The present invention relates to a magnetic nondestructive inspection device comprising:

an apply coil for generating an alternate magnetic field of variable frequency, an exciting power source for exciting said apply coil, at least one magnetic sensor means including a pair of magnetic sensors for detecting orthogonal vector components (X, Y) of a magnetic field generated from a test object, the vector components (X, Y) being parallel to the face of the apply coil, a detector means for detecting a signal of said magnetic sensor means, the detector means being located at a distance from the face of said apply coil and in proximity to said test object, a measurement means for measuring a detected signal having been detected by said detector means and a display means for analyzing a measured signal having been measured by said measurement means and performing an image processing for the measured signal and displaying the processed image.

The present invention relates to the magnetic nondestructive inspection device, the device further comprising an abnormality determination means for determining an abnormal current with respect to a normal current distribution.

The present invention relates to the magnetic nondestructive inspection device, wherein said test object is a structure having electrical conductivity.

The present invention relates to the magnetic inspection device, wherein said test object is a fruit and said device performs magnetic inspection on the maturity of the fruit.

The present invention relates to the magnetic inspection device, wherein said test object is a human body and said device performs magnetic inspection for a disorder of the human body.

The present invention is proposed for the purpose of solving the above-described problems, and a first aspect of the present invention relates to a magnetic impedance measurement device comprising an apply coil for generating an alternate magnetic field of variable frequency, a power source for the apply coil, at least one magnetic sensor means including a pair of magnetic sensors for detecting orthogonal vector components of a magnetic field generated from a test object, the vector components being parallel to the face of the apply coil, a measurement circuit for the magnetic sensor for detecting a signal of said magnetic sensor means, the measurement circuit being located at a distance from the face of the apply coil and in proximity to said test object, a lock-in amplifier circuit for detecting from an output of said measurement circuit a signal having the same frequency as that of said apply coil and an analysis means for analyzing an intensity and a phase change of an output of said magnetic sensor means with the use of an output signal of said lock-in amplifier circuit.

A second aspect of the present invention relates to the magnetic impedance measurement device, the device comprising a distance measurement means for measuring a distance between said apply coil or said one pair of magnetic sensor means and said test object.

A third aspect of the present invention relates to the magnetic impedance measurement means, the device comprising a scanning means for moving said test object in a direction parallel to or in directions parallel and vertical to the face of said apply coil as well as for fixing the test object.

A fourth aspect of the present invention relates to the magnetic impedance measurement device, wherein the device comprises, as an analysis means for analyzing an intensity and a phase of an output of said magnetic sensor means on the occasion of a measurement of said test object, a means that analyses an intensity and a phase of an output of said magnetic sensor means in the absence of said test object before or after the measurement of said test object, and analyzing a change from an intensity and a phase in the presence of said test object.

A fifth aspect of the present invention relates to the magnetic impedance measurement device, wherein a plurality of said apply coil or said magnetic sensor means each including a pair of magnetic sensors are provided, the magnetic sensor means being located at an equal distance from each other.

A sixth aspect of the present invention relates to the magnetic impedance measurement device, wherein a composite magnetic field of a plurality of frequencies is generated at said apply coil by means of said power source for the apply coil and said lock-in amplifier circuit is provided for each of the plurality of frequencies.

A seventh aspect of the present invention relates to the magnetic impedance measurement device, wherein said apply coil is a pair of opposed-type apply coils and said test object is placed between said opposed-type apply coils.

A eighth aspect of the present invention relates to the magnetic impedance measurement device, wherein said magnetic sensor is a Hall sensor, a magnetoresistive sensor, a magnetic impedance effect sensor, a flux gate or a superconducting quantum interference device.

A ninth aspect of the present invention relates to a magnetic impedance change determination means for imaging an induced current in said test object to determine an abnormality of the current distribution with the use of the magnetic impedance device according to any one of the first to eighth aspects.

Effect of the Invention

According to the first aspect of the present invention, an induced current can be generated in the test object by means of the apply coil. Hereinafter the central axis of the apply coil will be defined as the z axis, while the coil face will be defined as the xy plane defined by the orthogonal x and y axes. The x and y components of the component of the magnetic field parallel to the face of the apply coil of a magnetic field further generated from the induced current are each measured by means of detecting magnetic sensors. With respect to the magnetic distribution of the tangential component, the intensity distribution of the tangential component equivalently corresponds to the current distribution, because the intensity of the tangential component is large directly above the current. In addition, the magnetic field generated from the induced current has the same phase as that of the current. In such a way, a signal corresponding a local impedance characteristic of the test object can be obtained from the measured intensity and phase of the tangential component of the magnetic field. Further, since changes in the dielectric constant or the electrical conductivity of various test objects in response to a frequency change can be measured due to the variable frequency, it is possible to measure a change of the impedance in response to the frequency change. As for the magnetic field generated by the apply coil, the intensity of the component parallel to the apply coil axis, i.e. the z component, is the largest, while the x and y components are the smallest. Accordingly, the magnetic field generated by the apply coil entering into the magnetic sensor is quite large as compared to the magnetic field generated from the test object, with the result that it is necessary in the conventional art to provide a cancel coil for canceling the magnetic field from the apply coil near the magnetic sensor. In the present invention, however, because it is the x and y components with the smallest intensity of the magnetic field from the apply coil that are to be measured, there is no need for providing a cancel coil, which leads to a simpler configuration.

According to the second aspect of the present invention, in the case of measuring a magnetic response characteristic of the test object, the magnetic change varies substantially, depending on the distance between the apply coil and the test object and on the distance between the magnetic sensor and the test object. Specifically, in the case of measuring the current distribution, accurate analysis of the current distribution is not possible if the distance between respective measuring points and the magnetic sensor changes. However, by providing a distance measurement means for measuring the distance between the apply coil and the magnetic sensor, measurement of the current distribution can be made with improved accuracy.

According to the third aspect of the present invention, it is possible to measure the current distribution of the test object only with a single pair of magnetic sensors because the test object can be moved.

According to the fourth aspect of the present invention, an accurate measurement can be carried out even if the intensity of the magnetic field generated from the induced current in the test object is small. There are a magnetic noise and the applied magnetic field entering into the magnetic sensor, besides the magnetic field from the test object. Accordingly, a considerable error may be caused if a signal from the test object is weak and no more than the noise. However, true changes in the magnetic field vectors can be analyzed by measuring beforehand the output of the magnetic sensor in the absence of the test object before or after the measurement and deducting the magnetic field vector in the absence of the test object from the magnetic field vector obtained from the output of the magnetic sensor in the measurement of the test object.

Further, according to the fifth aspect of the present invention, due to a plurality of magnetic sensor means each including a pair of magnetic sensors, the sensor means being located at equal distance from each other, a measurement of the current distribution can be performed at high speed because a simultaneous measurement can be made at once for different measuring points without moving the test object.

According to the sixth aspect of the present invention, magnetic responses of the test object with respect to two different frequencies can be measured at once without switching between frequencies, since, instead of changing the frequency of the applied magnetic field, a composite magnetic field of a plurality of frequencies is generated and the output of the magnetic sensor is phase-detected using the plurality of frequencies.

According to the seventh aspect of the present invention, a uniform distribution of the applied magnetic field can be achieved over a wide area of the test object by providing a pair of opposed-type apply coils as the apply coil. Thus, a uniform magnetic signal can be obtained even in a case where the test object ranges over a wide area so that a measurement of a local change of the impedance characteristic of the test object is possible with high accuracy.

Further, according to the eighth aspect of the present invention, a magnetic response can be detected with an applied alternate magnetic field of a low frequency, with the use of a Hall sensor, a magnetoresistive sensor, a magnetic impedance effect sensor, a flux gate or a superconducting quantum interference device as a magnetic sensor. Preferably with the use of a magnetoresistive sensor, a magnetic impedance effect sensor, a flux gate or a superconducting quantum interference device, a local change in the impedance characteristic of the test object can be detected with an applied alternate magnetic field of a low frequency, from 1 kHz to below some Hz.

According to the ninth aspect of the present invention, since a local change in the impedance characteristic of the test object can be measured with high sensitivity with the use of the magnetic inspection device according to any one of the first to eighth aspects, it is possible to determine with high accuracy a structural defect in the test object, an impedance change in the biomedical tissue caused by disorders or a change in the maturity or density of farm products.

According to the present invention, the distribution of a magnetic field generated from an induced current in the test object is measured, and the distribution of the induced current can be analyzed with the use of the obtained distribution of the magnetic field.

Further, according to the present invention, the induced current in the test object can be imaged by means of the magnetic impedance device to determine an abnormality of the current distribution.

In addition, according to the present invention, since the current distribution can be imaged by measuring the magnetic field vertical to the applied magnetic field, it is possible to analyze even a local change of the current distribution caused at a defective portion so as to determine the location and the size of the defective portion.

1 apply coil
2 power source for the apply coil
3 current source
4 oscillator
5 a pair of magnetic sensor means
6 measurement circuit for the magnetic sensor
6-1 measurement circuit for the magnetic sensor
6-2 measurement circuit for the magnetic sensor
6-3 measurement circuit for the magnetic sensor
6-4 measurement circuit for the magnetic sensor
7 lock-in amplifier circuit
8 test object
9 analysis means
10 magnetic sensor for Bx
11 magnetic sensor for By
12-1 high-pass filter
12-2 high-pass filter
13-1 amplifier
13-2 amplifier
14-1 circuit for phase detection
14-2 circuit for phase detection
14-3 circuit for phase detection
14-4 circuit for phase detection
15-1 low-pass filter
15-2 low-pass filter
15-3 low-pass filter
15-4 low-pass filter
16-1 in-phase output terminal
16-2 in-phase output terminal
16-3 in-phase output terminal
16-4 in-phase output terminal
16-5 in-phase output terminal
16-6 in-phase output terminal
17-1 90-degree phase shift
17-2 90-degree phase shift
18-1 90-degree phase output terminal
18-2 90-degree phase output terminal
18-3 90-degree phase output terminal
18-4 90-degree phase output terminal
18-5 90-degree phase output terminal
18-6 90-degree phase output terminal
19 distance measurement means
20 scanning means
22-1 opposed-type apply coil
22-2 opposed-type apply coil
23 multi-channel magnetic sensor array
24 measurement circuit for multi-channel
25 lock-in amplifier circuit for multi-channel

BEST MODES FOR CARRYING OUT THE INVENTION

Preferred embodiments of the present invention will be described hereinafter in detail with reference to the accompanying drawings.

Embodiment 1

Figure 1:
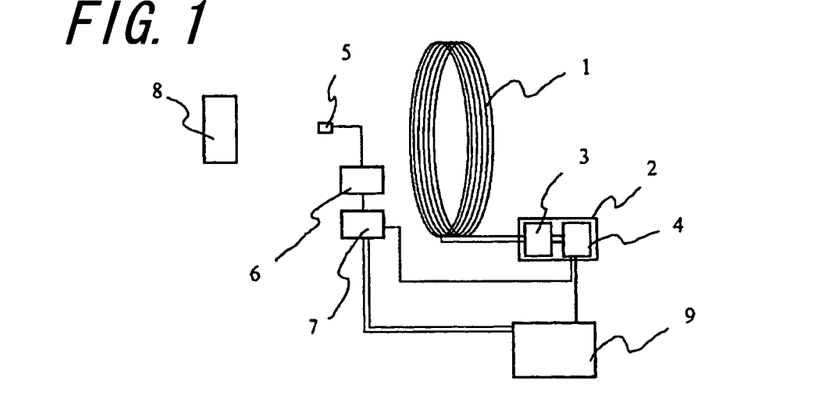
FIG. 1 is a schematic diagram showing a basic configuration of a magnetic impedance measurement device according to the present invention.
Figure 2:
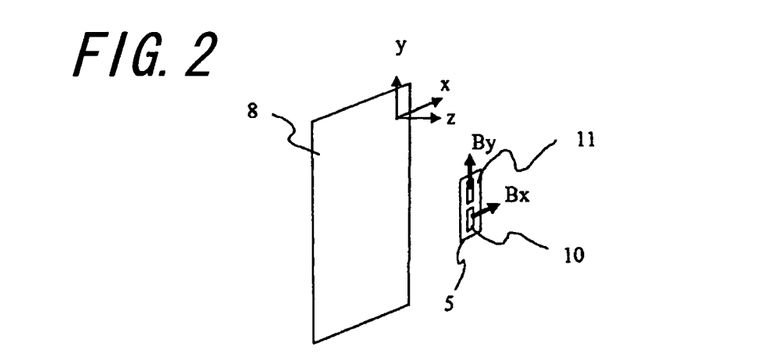
FIG. 2 is a schematic diagram showing magnetic field components to be measured by a pair of magnetic sensors of the magnetic impedance measurement device according to embodiment 1 of the present invention.

FIG. 1 is a schematic diagram showing a basic configuration of a magnetic impedance measurement device according to the present invention. A magnetic field is applied to the test object 8 by means of an apply coil 8. A power source 2 for the apply coil is adapted to change the frequency of the applied magnetic field by means of an oscillator 4. A current source 3 is driven with this signal to apply an alternate current to the apply coil 1. An induced current is generated in the test object 8 by the applied magnetic field and the induced current in turn generates another magnetic field. This magnetic field generated from the induced current is detected with a pair of magnetic sensor means 5 comprising magnetoresistive sensors. Here the coil face of the apply coil will be defined as the xy plane, while the central axis of the coil will be defined as the z axis. The one pair of magnetic sensor means 5 is provided, as shown in FIG. 2, with a magnetic sensor 10 for Bx and a magnetic sensor 11 for By for measuring two orthogonal magnetic field components, Bx and By, parallel to the xy plane. As a matter of course, other sensors such as a magnetic impedance effect sensor, a flux gate, a superconducting quantum interference device may also used as a magnetic sensor. Here, besides the magnetic field from the test object 8, there are magnetic noises of the environment including terrestrial magnetism entering into each of the magnetic sensor 10 for Bx and the magnetic sensor 11 for By, and the applied magnetic field also enters into the magnetic sensor. For this reason, a lock-in phase detection is carried out in which only a signal being synchronized with the frequency of the applied magnetic field is captured so that the magnetic field from the test object 8 only can be detected.

Figure 3:
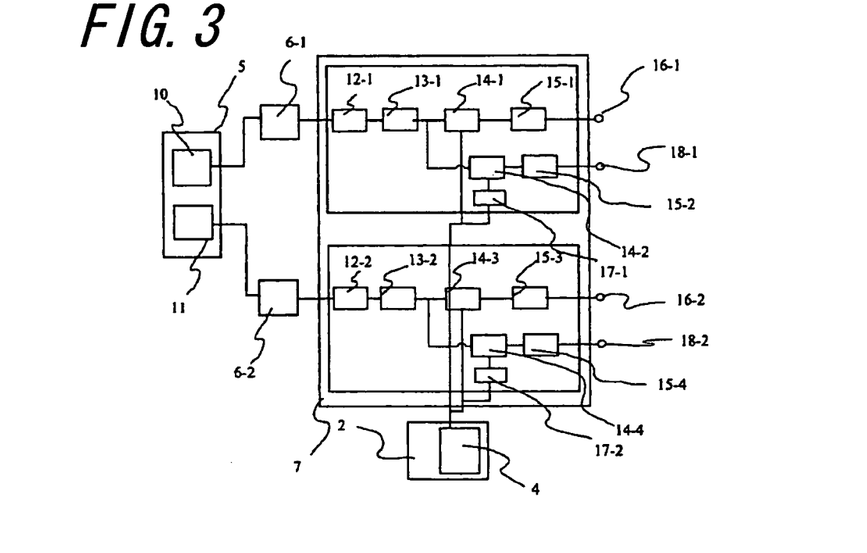
FIG. 3 is a schematic diagram showing a configuration of a lock-in amplifier of the magnetic impedance measurement device according to embodiment 1 of the present invention.

FIG. 3 shows a schematic diagram showing a lock-in amplifier of the magnetic impedance measurement device according to the present invention. The magnetic sensor 10 for Bx and the magnetic sensor 11 for By are driven respectively by a measurement circuit for the magnetic sensor 6-1 and a measurement circuit for the magnetic sensor 6-2, the outputs thereof being phase-detected by means of the lock-in amplifier circuit 7. The lock-in amplifier circuit 7 only detects signals being synchronized with the frequency that the oscillator 4 is applying to the apply coil. A signal having the same phase with respect to the signal of the oscillator 4 and a signal having a 90-degree shifted phase are separately detected. The output of the measurement circuit for the magnetic sensor 6-1 is amplified by means of an amplifier 13-1 after a direct current component is cut away by means of a high-pass filter 12-1, which is located at a first stage of the lock-in amplifier circuit 7. The output signal is then split into two different paths, one of which being phase-detected by means of a phase detection circuit 14-1 with respect to the signal having the same phase as the phase of the signal of the oscillator 4 and output via a low-pass filter 15-1 to an in-phase output terminal 16-1.

The other of the split signals passes through a phase detection circuit 14-2 in which the signal from the oscillator has been phase-shifted by 90 degrees by means of a 90-degree phase shift 17-1, and through a low-pass filter 15-2 to be output to a 90-degree phase shift output terminal 18-1. The magnetic response signal of the test object is split in this way into an in-phase signal and a 90-degree shifted signal. By splitting the signal into the two signals having phases different from each other by 90 degrees, a change in the intensity and the phase of the signal of the induced current in response to a change in the impedance characteristic of the test object can be obtained.

Embodiment 2

Figure 4:
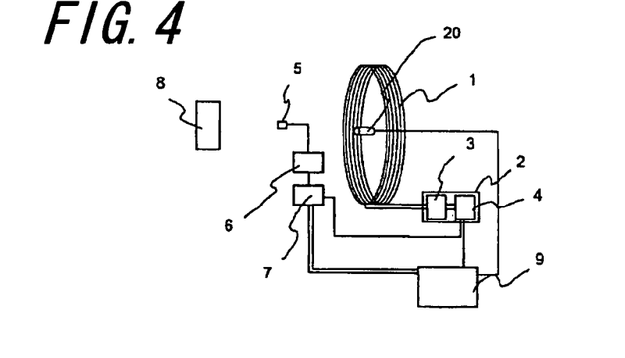
FIG. 4 is a schematic diagram showing a basic configuration of the magnetic impedance measurement device according to embodiment 2 of the present invention.

FIG. 4 is a schematic diagram showing a basic configuration of the magnetic impedance measurement device according to a second embodiment of the present invention. In embodiment 2, there is provided a distance measurement means 20 for the purpose of determining the positions of the test object 8 and the apply coil 1. The distance measurement means 20 may be placed anywhere, either in proximity to the apply coil 1 or in proximity to the one pair of the magnetic sensor means 5, as long as the relative distances of the distance measurement means 8 with respect to the apply coil 1 and the pair of the magnetic sensor means 5 is known. Here a distance meter with the use of a laser beam is used as the distance measurement means. The magnetic response characteristic of the test object 8 with respect to the applied magnetic field varies depending on the distance from the apply coil 1, and also the intensity of the signal varies substantially depending on the distance from the pair of magnetic sensor means 5 for detecting the magnetic response characteristic. For this reason, measurements with repeatability can be achieved by providing the distance measurement means 20.

Embodiment 3

Figure 5:
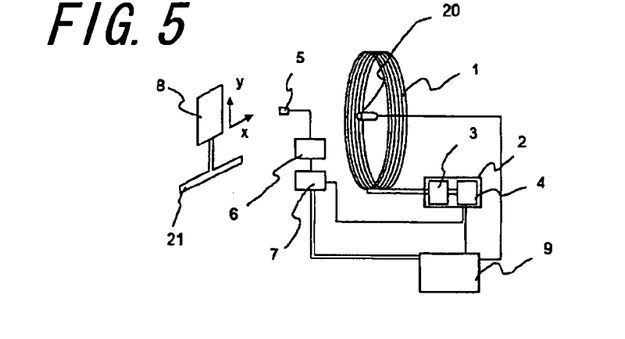
FIG. 5 is a schematic diagram showing a basic configuration of the magnetic impedance measurement device according to embodiment 3 of the present invention.

FIG. 5 is a schematic diagram showing a basic configuration of the magnetic impedance measurement device according to embodiment 3 of the present invention. Here the device according to embodiment 2 is provided with a scanning means 21 for the test object and the distance between the pair of the magnetic sensor means and the test object can be held constant by means of a distance measurement means and measurement can be made on the test object with a scanning movement. With this mechanism, the distribution of a magnetic field generated from an induced current of the test object can be measured by means. Further, it is possible to analyze the distribution of the induced current from the distribution of the magnetic field.

Figure 6:
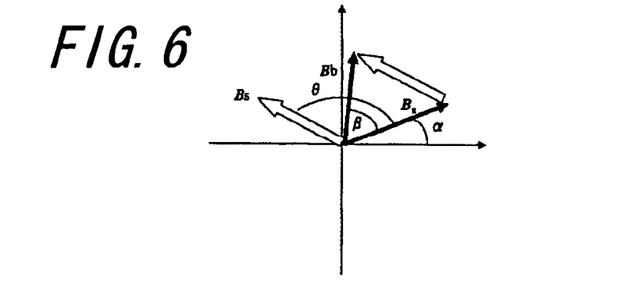
FIG. 6 is a diagram showing a relation of magnetic field vectors according to a measurement result of embodiment 3 in a case of measuring the magnetic field vector and the test object in the absence of the test object.

FIG. 6 is a pattern diagram of a basic processing method for an output from the magnetic sensor having been subjected to a lock-in phase detection. An output from the magnetic sensor in the absence of the test object is defined as Ba. Because of an inductance of the apply coil 1, the phase is shifted depending on a frequency by a from the phase of the signal from the oscillator of the current source. Measuring the test object 8, the phase is further shifted by β depending on the impedance characteristic thereof. Defining the signal vector at this time as Bb, the magnetic field signal vector generated from the induced current in the test object can be represented as Bs=Bb−Ba. By translating this vector to the origin, a phase angle θ is obtained. Here, the phase angles such as α, β and θ vary depending on the frequency. For this reason, a magnetic vector intensity |Ba| and a phase angle α in the absence of the test object 8 are measured before the measurement or after the measurement. An intensity |Bs| and a phase angle θ of a magnetic signal vector generated eventually from the induced current can be obtained from the magnetic vector intensity and the phase angle in the absence of the test object and also a magnetic vector intensity |Bb| and a phase angle β obtained in measuring the test object. In the conventional method, a cancel coil is used to make very small the magnetic field vector detected in the absence of the test object so that only the signal from the test object 8 can be analyzed. In this analyzing method, however, the signal from the test object 8 can be analyzed without any use of cancel coil, because information of the magnetic vector is obtained in the absence of the test object.

Figure 7:
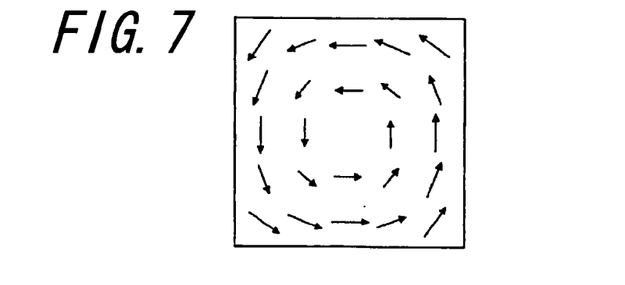
FIG. 7 is a diagram of the current distribution in the test object according to an analysis result of embodiment 3.

FIG. 7 shows a result of a measurement and an analysis on a copper plate having a dimension of 10 cm by 10 cm and a thickness of 1 mm, with the use of the magnetic impedance measurement device according to embodiment 3 of the present invention and the above-described method of analysis. FIG. 3 represents a current distribution of an induced current in the copper plate. Arrows shown in the figure represent results of an analysis of current vectors obtained from measurements at each point with movement of the copper plate as the test object by means of the scanning means and analyses of the measurement results. A signal vector of the copper plate can be represented as Bs=|Bx|ex+|By|ey, dividing it into the x and y components. Here, ex and ey represent the unit vectors in the x and y directions, respectively. Using this signal vector, the current can be represented as Is ∝|Bx|ey−|By|ex. FIG. 7 shows such current vectors Is. Referring to this figure, it is possible to know the direction and the intensity of the induced current in the copper plate at each measuring point. Analysis and imaging can be performed in this way and the results can be displayed.

Embodiment 4

Figure 8:
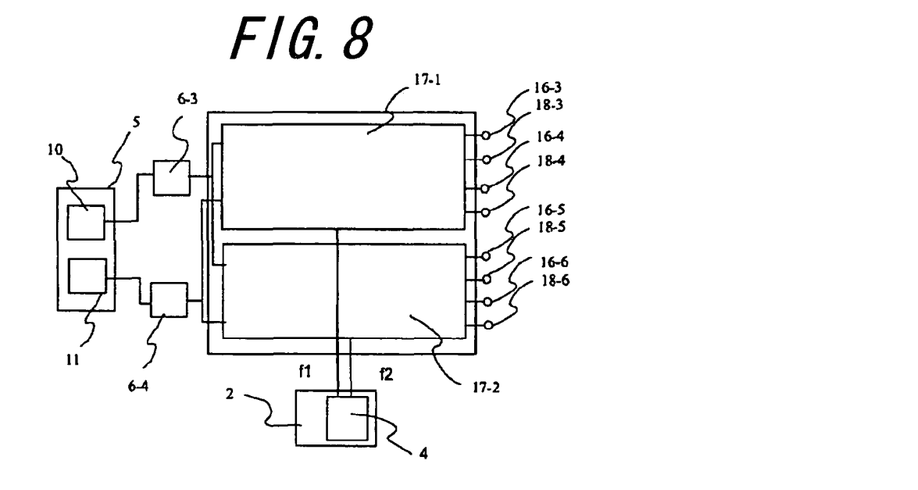
FIG. 8 is a schematic diagram showing a configuration of the lock-in amplifier of the magnetic impedance measurement device according to embodiment 4, with the use of a composite applied magnetic field of two frequencies.

FIG. 8 shows the magnetic impedance measurement device according to embodiment 4 of the present invention. While the measurement is carried out with switching of the frequency, the apply coil is supplied with a composite current wave pattern consisting of two frequencies f1 and f2, which are simultaneously generated by means of the oscillator 4 of the power source 2 for the apply coil. For this reason, the outputs from the measurement circuit for the magnetic sensor 6-3 and the measurement circuit for the magnetic sensor 6-4 each connected to the respective magnetic sensors are split into two paths and lock-in amplifier circuits are provided for each of the frequencies f1 and f2. Accordingly, there are four signals obtained at once with respect to the frequency f1, at output terminals of an in-phase output terminal 16-3, an in-phase output terminal 16-4, a 90-degree phase shift output terminal 16-5 and a 90-degree phase shift output terminal 16-6. There are consequently eight signals from a single pair of magnetic sensor means comprising a magnetic sensor 10 for the x component and a magnetic sensor 11 for the y component. With this, a change of the impedance characteristic of the test object in response to the frequency change can be measured without switching between different frequencies.

While description has been made above with respect to detection devices comprising a single apply coil, a uniformity of the applied magnetic field over a greater area is required if the test object is large or in a case where it is necessary to apply a uniform magnetic field to the test object. Embodiments will be described hereinafter in which a uniform alternate magnetic field can be applied.

Embodiment 5

Figure 9:
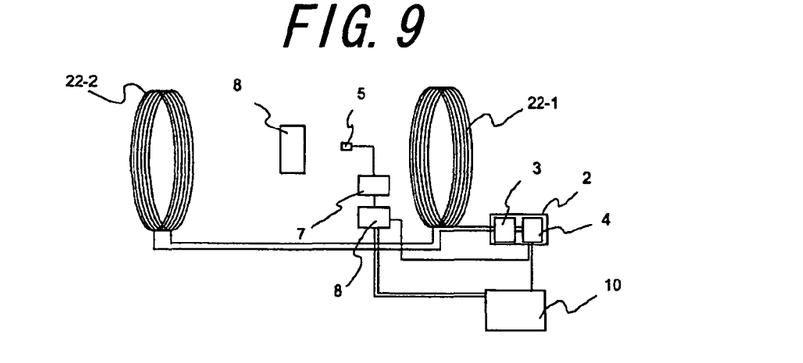
FIG. 9 is a schematic diagram showing a basic configuration of embodiment 5 of the present invention with the use of opposed-type apply coils.

FIG. 9 is a schematic diagram showing a basic configuration according to the fifth embodiment of the present invention with the use of opposed-type apply coils. In embodiment 5, there are provided two apply coils, an opposed-type apply coil 22-1 and an opposed-type apply coil 22-1, the coil face of one coil facing the coil face of the other. This is a combination of the coils well known as the Helmholtz coil, with the use of which measurement can be made for a larger test object 8.

Embodiment 6

Figure 10:
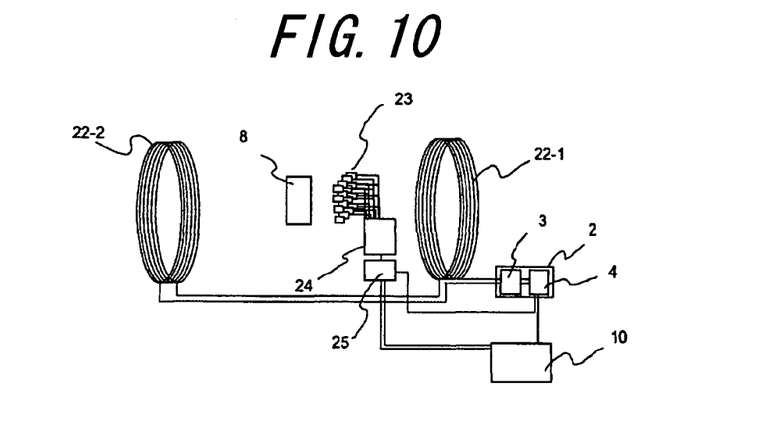
FIG. 10 is a schematic diagram showing a basic configuration of embodiment 6 of the present invention with the use of opposed apply coils and a plurality of magnetic sensors.

FIG. 10 is a schematic diagram showing a basic configuration according to embodiment 6 of the present invention, with the use of opposed-type apply coils and a multichannel magnetic sensor array 23 comprising a plurality of pairs of magnetic sensor means. In embodiment 5, a single pair of magnetic sensor means is used and the scanning point is shifted by means of a scanning device. In embodiment 6, however, the device is adapted to simultaneously measure magnetic responses at different portions of the test object because multiple pairs of magnetic sensor means 5 are provided. For this reason, a multichannel measurement circuit 24 and a multichannel lock-in amplifier circuit 25 are provided in order to drive the multiple pair of magnetic sensor means 5 to carry out a simultaneous measurement. By providing a large number of magnetic sensors in this way, the measurement time can be drastically reduced and it is also possible to observe transitional phenomena.

It is obvious that the present invention is not limited to the embodiments described above and that various modifications and design variations are possible without departing from the spirit and the scope of the present invention.

INDUSTRIAL APPLICABILITY

The present invention relates to a device for applying an alternate magnetic field to the test object and detecting the impedance characteristic thereof and also for imaging the distribution of the induced current. The present invention relates to a device for applying an alternate magnetic field to the test object and detect the impedance characteristic thereof by means of a magnetic sensor. Therefore, the device can be used as, for example, a nondestructive inspection device for detecting a defect in a electrically conductive structure, a device for testing the maturity and the density of fruits or the like and a bioelectrical impedance inspection device for testing for example an impedance change inside the human body due to a disorder.

The invention claimed is:

1. A magnetic impedance measurement device comprising:
   an apply coil for generating an alternate magnetic field of variable frequency, said apply coil being arranged at a distance from a test object,
   an exciting power source for exciting said apply coil,
   a pair of magnetic sensor means for detecting orthogonal vector components (X, Y) of a magnetic field generated from the test object, the vector components (X, Y) being parallel to a face of the apply coil, said face of the apply coil being perpendicular to a central axis of said apply coil, said pair of magnetic sensor means being arranged between said face of the apply coil and said test object at a distance from the face of the apply coil and in proximity to said test object,
   a measurement means for measuring a detected signal having been detected by said pair of magnetic sensor means, and
   an analysis means for synthesizing the detected vector components (X, Y) and imaging an induced eddy current in said test object.

2. A magnetic impedance measurement device according to claim 1, the sensor means being movable so as to approach said test object.

3. A magnetic impedance measurement device according to claim 1, further comprising an analysis means for analyzing a measured signal having been measured by said measurement means and performing an image processing for the measured signal and displaying the processed image.

4. A magnetic impedance measurement device according to claim 1, the device further comprising a lock-in amplifier circuit for detecting from an output of said measurement means a signal having the same frequency as the frequency of said apply coil.

5. The magnetic impedance measurement device according to claim 4, the device further comprising an analysis means for analyzing intensity and phase changes of an output of said magnetic sensor means with the use of an output signal of said lock-in amplifier circuit.

6. A magnetic impedance measurement device according to claim 1, the device further comprising a scanning means for moving said test object in a plane parallel to the face of said apply coil as well as for fixing said test object.

7. The magnetic impedance measurement device according to claim 1, wherein the plurality of said magnetic sensor means each comprise a pair of magnetic sensors, the magnetic sensor means being located at an equal distance from each other.

8. The magnetic impedance measurement device according to claim 1, wherein a composite magnetic field of a plurality of frequencies is generated at said apply coil by means of said power source for the apply coil and a lock-in amplifier circuit is provided for each of the plurality of frequencies.

9. The magnetic impedance measurement device according to claim 1, wherein said apply coil is a pair of opposed-type apply coils and said test object is placed between said opposed-type apply coils.

10. The magnetic impedance measurement device according to claim 1, wherein said magnetic sensor means is a Hall sensor, a magnetoresistive sensor, a magnetic impedance effect sensor, or a flux gate or a superconducting quantum interference device.

11. A magnetic impedance measurement device according to claim 1, further comprising a scanning device for moving said test object.

12. A magnetic impedance measurement device according to claim 1, wherein a plurality of said pairs of magnetic sensor means forms a multichannel magnetic sensor array.

13. A magnetic nondestructive inspection device comprising:
   an apply coil for generating an alternate magnetic field of variable frequency, said apply coil being arranged at a distance from a test object,
   an exciting power source for exciting said apply coil,
   at least one magnetic sensor means including a pair of magnetic sensors for detecting orthogonal vector components (X, Y) of a magnetic field generated from the test object, the vector components (X, Y) being parallel to a face of the apply coil and the magnetic sensor means being located at a distance from the face of said apply coil and in proximity to said test object,
   a measurement means for measuring a detected signal having been detected by the magnetic sensor means, and
   an analysis means for synthesizing the detected vector components (X, Y) and imaging an induced eddy current in said test object.

14. The magnetic nondestructive inspection device according to claim 13, wherein said test object is a structure having electrical conductivity.

15. The magnetic inspection device according to claim 13, wherein said test object is a fruit and said device performs magnetic inspection on the maturity of the fruit.

16. The magnetic inspection device according to claim 13, wherein said test object is a human body and said device performs magnetic inspection for a disorder of the human body.

* * * * *